United States Patent [19]
Litvak et al.

[11] Patent Number: 5,414,504
[45] Date of Patent: * May 9, 1995

[54] INTERFERENCE REMOVAL

[75] Inventors: Herbert E. Litvak, Palo Alto; Steven C. Leach, Santa Clara; Edward G. Rodgers, Mountain View, all of Calif.

[73] Assignee: Xinix, Inc., Santa Clara, Calif.

[*] Notice: The portion of the term of this patent subsequent to May 4, 2010 has been disclaimed.

[21] Appl. No.: 19,748

[22] Filed: Feb. 19, 1993

Related U.S. Application Data

[63] Continuation of Ser. No. 526,558, May 18, 1990, Pat. No. 5,208,644.

[51] Int. Cl.6 .............................................. G01N 23/22
[52] U.S. Cl. .................................. 356/72; 204/192.32; 204/192.34; 250/227.23
[58] Field of Search .................. 356/72, 357, 73, 369, 356/430, 435; 250/227.23; 204/192.32, 192.34

[56] References Cited

U.S. PATENT DOCUMENTS 4,611,919  9/1986  Brooks, Jr. et al. ............... 356/357

Primary Examiner—Vincent P. McGraw
Attorney, Agent, or Firm—Majestic, Parsons, Siebert & Hsue

[57] ABSTRACT

An improved method for minimizing interferences from random noise and correlated fluctuations which obscure electrical signals converted from optical emissions. In particular, an improved method for the removal of interferences from optical emission signals during endpoint determination in dry etching processes for the fabrication of microelectronic devices which derives information in the presence of random noise, correlated fluctuations and periodic modulations of the plasma by maximizing the signal to random noise ratio and minimizing the obscuring effects of correlated fluctuation.

28 Claims, 4 Drawing Sheets

INTERFERENCE REMOVAL

This is a continuation of application Ser. No. 07/526,558, filed May 18, 1990, U.S. Pat. No. 5,208,644.

BACKGROUND OF THE INVENTION

1. Field of the Invention

This invention relates generally to the use of optical devices to sense the progress of processes, transmit signals related to such progress, detect such signals and extract from such signals information to control such processes. More particularly, this invention relates to the removal of interferences from optical emission signals during endpoint determination in dry etching processes for the fabrication of micro-electronic devices, including, but not limited semiconductor devices, and for other micro-machining processes, which are accompanied by the emission of light from the reactants, products, film being etched or some combination thereof.

BRIEF DESCRIPTION OF THE PRIOR ART

Photolithography makes it possible to transfer a desired circuit pattern to a surface of a semi-conductor device. This is commonly done by the application of a photoresist film to a wafer followed by imaging and developing processes which form the desired pattern upon the wafer.

The wafer is then etched in the pattern formed by the developing processes. Dry etching, which is the chemical processing of microcircuit films in a low pressure reactor, is achieved by a variety of dry etch processes, including, but not limited to, plasma etch, reactive ion etch, ion milling, reactive ion beam etch, magnetron etch, and downstream etch. Gases, such as Carbon Tetrafluoride and others are fed into a plasma reactor and a high frequency discharge is used to convert the gases into reactive ions and molecular fragments which react with the film being etched.

During the etching steps it is important to monitor the progress of the etch and to detect the point at which the underlying material or film being etched is reached. This point is called the endpoint although the process may continue for a period after endpoint, which is referred to as overetching.

Optical emission spectroscopy is a current method used to detect process endpoint in plasma etching systems. This is possible because the plasma excites certain molecular species and causes them to emit light of wavelengths that are characteristic of each species being etched. In an optical monitoring system specific wavelengths of the light emitted from the plasma are selected and fed to detectors, such as photodiodes, photomultipliers, and array detectors which convert the light intensities into electrical signals. It is known that the intensity of the detected raw signals is related to the level of light detected and by selecting wavelengths which correlate to the reaction products of the particular process, the process may be monitored either at specific wavelengths are at all wavelengths by a spectral scan. In particular, by selecting a wavelength which corresponds to the emissions generated by the layer below the layer which is being etched, the point at which that layer is reached may be easily detected. When the film being etched has completely cleared from the underlying material or film, there is a chemical change both in the gas phase and on the film. Product species from the film are no longer being generated, and some reactants increase because they are no longer being consumed by the reaction. These chemical changes show up as changes in optical emission intensities. Thus by continuously monitoring the intensity of an appropriate emission feature, either a reactant or product of the etch reaction, a change in emission intensity generally signals removal of the film being etched and contact of the etching agent with the underlying material or film, or endpoint. The change in emission intensity which signals endpoint may either be an increase for a reactant emission or a decrease for a product emission or the presence of another reactant emission.

However, in some processes, the change in the optical emission signal being monitored for endpoint is small and difficult to detect. Where the signal or signal change at endpoint is small, the presence of interfering signals may obscure the signal or signal change and prevent the observation of endpoint or cause false endpoints to be read. Interferences may result from a number of sources. These include, but are not limited to the following:

(1) process related interferences which naturally occur in the chemical stirring of the plasma, and which may be manifested in plasma fluctuations and signal drift;

(2) Equipment created variations, which result from the actions of the operator in controlling the process, such as control loops and similar activities which are inherent in the normal operation of etching machines to stabilize flow, pressure, power, temperature or other variables;

(3) The practice in certain plasma etch machines of introducing a periodic variation in plasma density via an external magnetic field, or by modulating the RF power into the plasma or other means. These machines produce a low frequency, typically 0.1 to 100 HZ, periodic modulation of the plasma in the etch chamber.

In plasma etch machines such modulation may show up as a periodic oscillation in the optical emission signal and is often of a magnitude large enough to overwhelm the relatively small emission signal change at endpoint. Another obstacle to detecting endpoint in such systems or to perform plasma or process diagnostics based on the measuring of optical emission intensities is the superimposition of the oscillation on spectral scans, i.e. signal vs. wavelength, of the plasma emission.

(4). Plasma emissions from other species at or near the wavelength being monitored.

All of the interferences described above are frequently of a broad-band nature, i.e. occur at a variety of spectral wavelengths. To the extent this is true, optical emission intensities measured at two separate wavelengths will be partially correlated. There will be intensity fluctuations that are common to both wavelengths, because their cause is a common perturbation of the plasma. This correlation provides a vehicle for interference removal by simultaneous observation of two or more wavelengths and suitable combinations of the emission intensities.

The principal object of this invention is a method to monitor etch processes and to determine endpoints in plasma etch chambers in the presence of interferences which tend to obscure the signals which indicate the changes which are to be detected and observed.

Another object of this invention is to monitor processes and to determine endpoints in plasma in the presence of a periodically varying low frequency plasma modulation.

Yet another object of this invention is a method and device to detect endpoints using optical emission spectroscopy in systems where the optical emission signal at endpoint is small relative to the signal caused by plasma fluctuation.

Still another object of this invention is a method and device for analyzing the signals emitted at different wavelengths from a plasma emissions and isolating those portions of the signals which are correlated as contrasted to those which are uncorrelated.

An additional object of this invention is to monitor processes in the presence of emission interferences caused by other species which omit at or near the wavelength being monitored.

Optical emission spectroscopy is based upon detecting and observing emission intensity changes at selected wavelengths. Ideally, changes in emission intensity would result from single isolated source, however, in reality a number of sources contribute to such changes. These may be broadly characterized as follows:

(1) Random noise, comprising both electronic noise, which is generally quite low in well-designed instruments, and shot noise, which is inherent in the process of converting a light signal to an electrical signal;

(2) Correlated fluctuations, including intensity drift, i.e., intensity changes which occur simultaneously at two or more wavelengths, as discussed above;

(3) Periodic modulations of the plasma;

(4) Intensity changes arising from the removal of a film layer from the wafer or substrate surface i.e. endpoint.

The changes resulting at endpoint are what we desire to unequivocally determine, but such changes are generally obscured by the interferences described in (1), (2) and (3) above.

In the practice of this invention, the electronic portion of random noise is removed or minimized by good electrical design and the shot noise portion is minimized by collecting a large amount of light from the etch chamber.

The intensity changes resulting from correlated fluctuations are removed or minimized by observing two or more wavelengths simultaneously, which experience such fluctuations, but only some of which experience the endpoint intensity changes. An algorithm which suitably combines the signal intensities from both channels, e.g., a simple subtraction of Channel B from Channel A, will remove the common or correlated intensity fluctuations leaving only the endpoint intensity change, which we detect using existing endpoint detection algorithms.

U.S. Pat. No. 4,312,732 issued to Degenkolb et al, Method for the Optical Monitoring of Plasma Discharge Processing Operations and the references cited therein teach the basic concepts of optical monitoring of plasma discharge.

SUMMARY OF THE INVENTION

This invention teaches the removal of interferences from optical emission signals generated in plasma etch machines by using emission spectroscopy to simultaneously look at two or more selected wavelengths, combining the signals resulting from such wavelengths into a resultant signal, and using algorithms to minimize the effects of plasma perturbations or fluctuations upon such signals.

In the practice of this invention, the electronic portion of random noise is removed or minimized by good electrical design and the shot noise portion is minimized by collecting a large amount of light from the etch chamber.

The intensity changes resulting from correlated fluctuations are removed or minimized by observing two or more wavelengths simultaneously, which experience such fluctuations, but only some of which experience the-endpoint intensity changes. An algorithm which suitably combines the signal intensities from both channels, e.g., a simple subtraction of Channel B from Channel A, will remove the common or correlated intensity fluctuations leaving only the endpoint intensity change, which we detect using existing endpoint detection algorithms.

It is not novel per se to look at two wavelengths in monitoring the endpoint detection signal generally, however heretofore the use of two wavelengths has not been deemed appropriate to improve endpoint detection in plasma chambers where the signal changes are small, such as when the exposed film area is less than 5%, The reasons that practitioners have deemed such an approach inappropriate are: the shot noise or electronic noise is of such intensity that any correlated signals have been obscured; the criticality of having the detectors both looking at substantially the same place has not been recognized; and the failure to recognize that other wavelengths would reveal correlated fluctuations. As a result of the above it has not been taught to look at other wavelengths for the purpose of eliminating or reducing sources of fluctuations and to enhance signal to noise ratios.

We have found that correlated signals may be detected by digital processing utilizing suitable lenses to increase the quantity of light collected and improving the quality of light collected by utilizing two or more fiber optic bundles, in which fibers from individual bundles are systematically positioned alternately adjacent to each other. Digital processing, such as median filtering will decrease the random noise more than linear filtering, and in combination with the increased light collection provided by suitable lenses lowers the relative value of the shot noise. The systematic positioning of the individual fibers in the fiber optic bundles as taught in co-pending application, "Light Collection Method and Apparatus" filed simultaneously with this application, allows both channels to look at the same target area. Although the concept of "looking at the same target" may seem elementary, we have found that fiber bundles which are placed side-by-side, rather than with alternating fibers as taught by this invention, "look" at targets which are sufficiently different that the correlations are masked and thus have not previously been recognized as a useful diagnostic tool.

Another important element of our invention is the recognition that the correlated signal may be separated from the uncorrelated signal by looking at specific wavelengths rather than at the entire spectrum.

An important aspect of this invention is the recognition that what heretofore has been characterized as noise has within it a portion that may be related with the progress of and the endpoint of a process. For purposes of our discussion when we refer to noise, we mean that portion of the signal which is not related to the endpoint of a process and thus is undesirable.

In those particular processes which use plasma modulation, there is yet another factor within the signal which must be considered. That factor is the portion of the signal which is related to the plasma modulation, but which does not naturally occur in the process. To achieve our purposes, the portion of the signal caused by plasma modulation must also be treated or removed.

Lastly, another obscuring factor is signal drift. Again, if the noise and plasma fluctuations are taken into account, but signal drift is not, the desired progress and endpoint indicators will not be readily apparent, even though they will exist within the generated signal.

In summary, the signals which indicate endpoint and/or process progress within a plasma etch chamber may be relatively so small that they are hidden within the raw signal which is a combination of random noise, correlated fluctuations, periodic modulations, and process related signal.

We have further found that the effect of any periodic modulation of the plasma modulation may be eliminated by averaging the optical emission signal over an integral number of plasma modulation cycles. This process effectively converts the signal into an unmodulated signal.

We have further found that the process related signals may be monitored and detected by simultaneously looking at two or more selected wavelengths and applying a suitable algorithm to combine the intensity changes at each wavelength to remove or greatly reduce the correlated fluctuations.

DETAILED DESCRIPTION OF THE INVENTION

The present invention is an improvement in an optical monitoring system for determining endpoints and performing plasma or process diagnostics of a dry etching process within the presence of optical emission signal interferences. The present invention maximizes signal to noise ratios and minimizes interference by the steps of:
  (a) measuring said electrical signal in separate channels at two or more wavelengths;
  (b) normalizing the separate electrical signals from said separate channels;
  (c) analyzing said signals for random noise, correlated fluctuations, and the dry process monitoring signal;
  (d) maximizing the signal to random noise ratio of the process monitoring signal; and
  (e) minimizing the obscuring effects of correlated fluctuations from the separate channels by algorithms. The resultant signal is no longer obscured by the random noise or correlated fluctuations.

Figure 1:
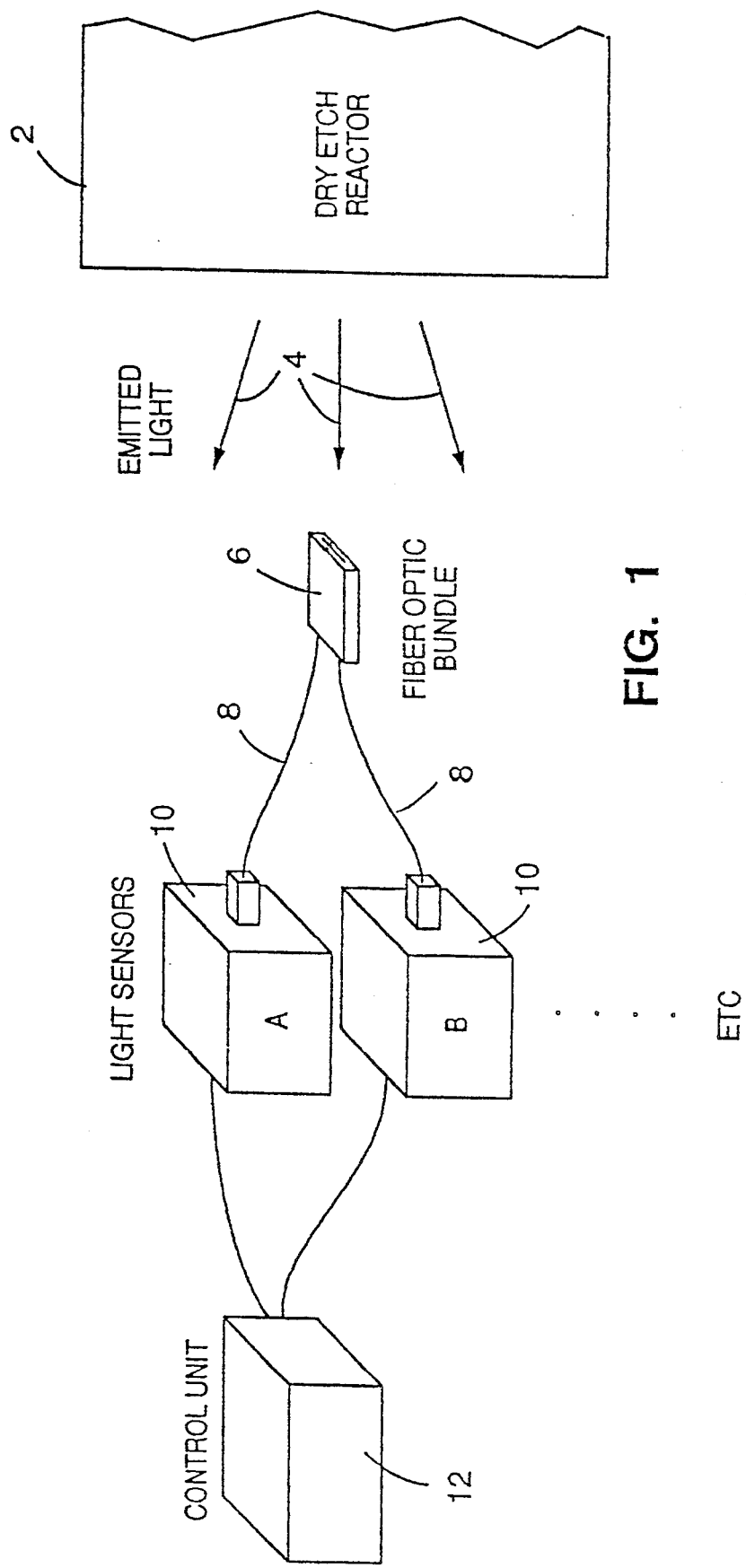
FIG. 1 is a schematic view of a device in accordance with this invention.

Referring to FIG. 1., A dry etch reactor 2 is the source of emitted light 4 which is transmitted to a fiber optic bundle 6. Fiber optic bundle 6 is bifurcated into multiple channels 8. In this example two channels are shown, but more may be used where desired. Channels 8 collect light from the same source and transmit it to separate light sensors 10 which in turn convert said light signals to electric signals which are processed within control unit 12, which may be an endpoint control detection device.

As stated above, endpoint detection may be masked by interferences which are large compared to the endpoint signal or by plasma fluctuations, either periodic or episodic. The improvements of this invention are useful under both of these conditions.

In processes where small signal changes are being masked by high levels of interference, we have found that endpoint determination using two or more fiber optic bundles to detect multiple wavelengths is significantly enhanced by mixing the fibers within the separate fiberoptic bundles to minimize any bias in the view of each fiber bundle. Although it is not unusual to place the separate fiberoptic bundles proximate each other, it has not been heretofore recognized that the interleaving of the bundles is significant. Particularly where the endpoint signal change is small relative to interferences, it is critical that the multiple wavelength detectors are looking at the same area. We believe that the interleaving of the fiberoptic bundles assures that the signals transmitted by each bundle are from substantially identical sources.

In processes where the interferences are periodically varying low frequency modulations, such as that intentionally provided by plasma etching machines, we have found that averaging of signals at any one wavelength over an integral number of plasma modulation cycles improves both monitoring of the process and endpoint detection.

Once the multiple signals have been detected we have found that combining them into a resultant signal using appropriate algorithms minimizes not only periodic plasma modulation interferences, but also minimizes plasma perturbations or fluctuations from other sources such as rotating wafer holders. In a system employing two different optical emission channels (Channel A and Channel B) the resultant signals resulting from use of the algorithms A-(N ×B), A/(N×B) or similar algorithms, where N is an adjustable scaling parameter constant, adjusted to naximize the signal to noise ratio of the resultant signal is effective to reveal endpoints which are masked if only the individual signals are observed.

Another element of the method of this invention is the normalization of the signal level of each channel to a reference value. In the practice of this invention a common reference signal level is empirically determined and then electronically driven automatic gain control circuits or other means are used to coarsely adjust each channel separately to such reference signal. In a process having periodic modulations integral averaging must also be performed. This step is followed by fine-tuned software scaling of the channels to the reference signal for precise normalization of the two channels at the beginning of each etch run.

Although we have and will primarily discuss interferences caused by etching machine modulation, fluctuations in signals which manifest themselves as interferences, may come from a variety of sources. For example, in batch processes where a large quantity of wafers are located upon a rotating table, the signal will vary dependent upon the location of a particular wafer relative to the optical window. In addition it is common within the fabrication of semiconductors, such as in track systems, to rotate individual wafers, in such a system, the signal will fluctuate because of the rotation. This invention is useful for the removal of interferences in all of these situations.

In an example of the practice of this invention, a semiconductor wafer, consisting of a silicon substrate with a thin (approximately 500 nm) film of Silicon dioxide covered by a photoresist mask with approximately 2-3% exposed area is etched in a plasma etcher, for the purpose of making small contact holes in the Silicon dioxide film. The light emitted from the plasma etcher during the etch is observed by an endpoint controller device, such as the Xinix Model 1200, having the capability of observing multiple wavelengths. One wavelength of light, viz. 483 nm,("Channel A") corresponding to an optical emission band of the molecule CO, is observed to detect the process endpoint, the point in time at which the exposed Silicon dioxide film has been etched away and the etch has reached the substrate. The CO emission decreases at this point, because there is less oxygen in the chamber to form CO, when the film disappears. A second wavelength of light, viz 485 nm, ("Channel B") is simultaneously observed during the etch to be used as a background or interference correction channel. A combined signal of the form A-(N×B) where A and B refer to the signal intensities of channels A and B, respectively, and N is an adjustable parameter, typically approximately 1, is examined to determine endpoint.

Figure 2:
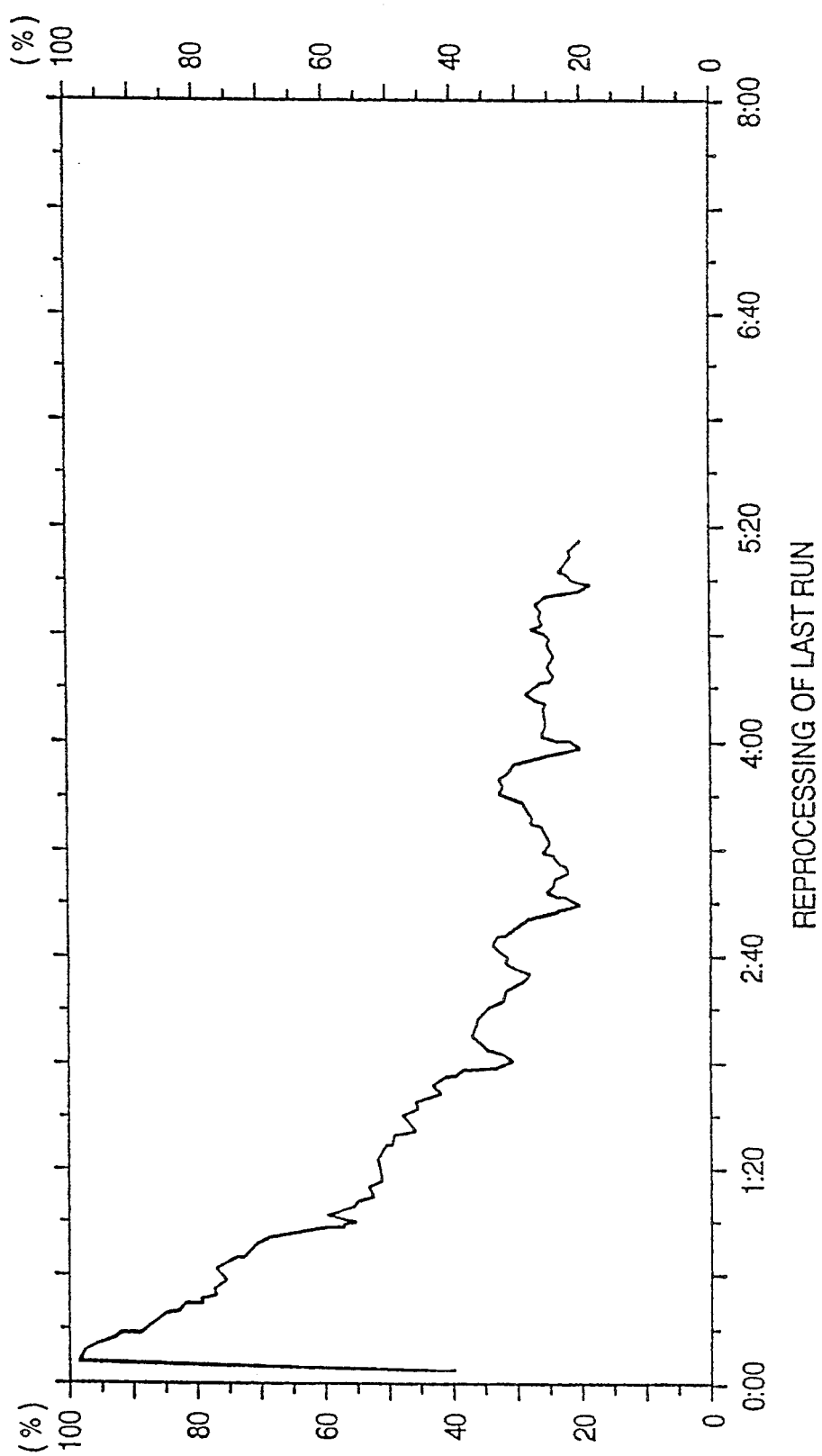
FIG. 2 is a graph of signal vs time of channel A of a dual channel system.

FIG. 2, shows the run data, signal vs time, from Channel A during the etch.

Figure 3:
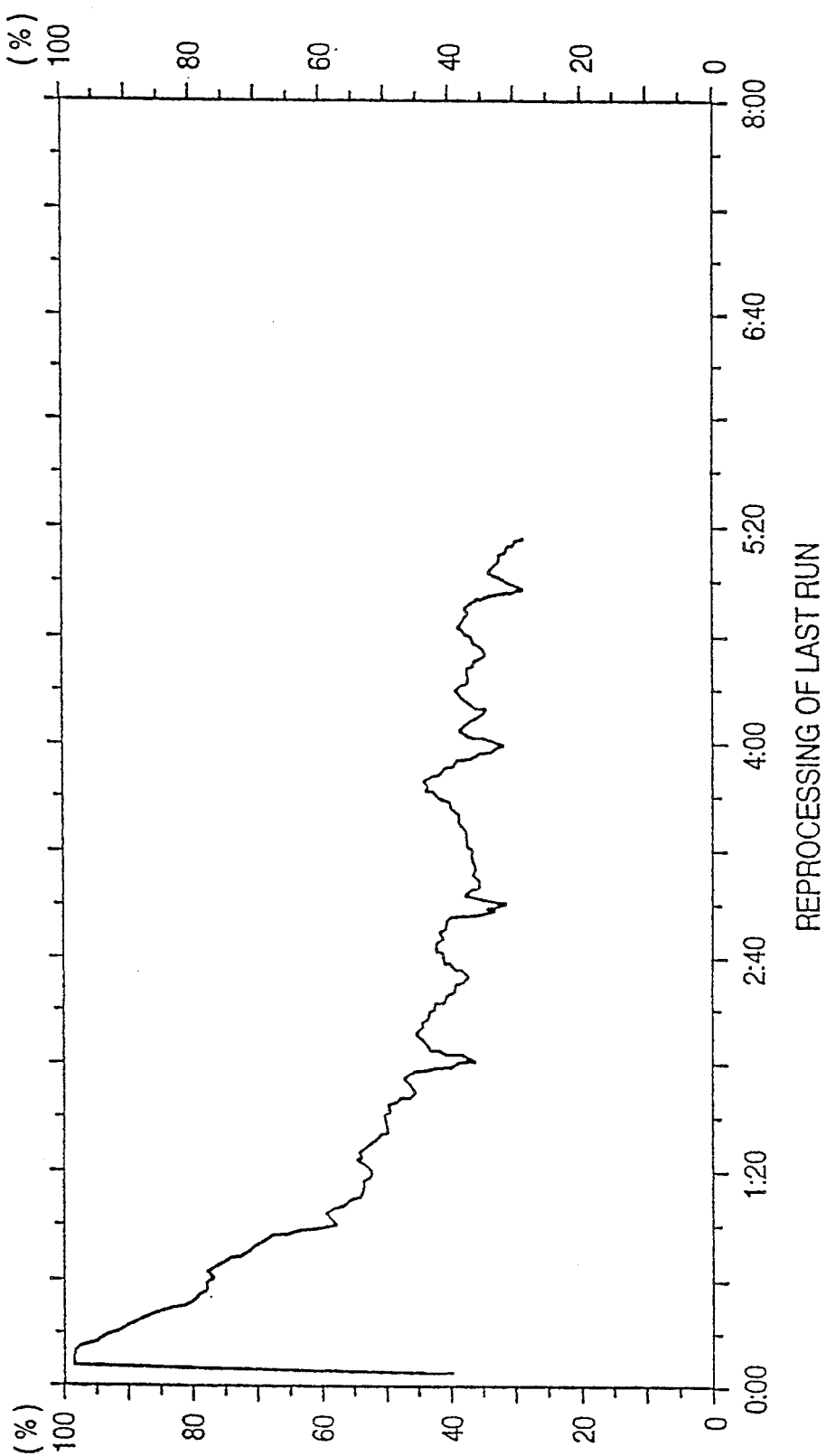
FIG. 3 is a graph of signal vs time of Channel B of a dual channel system.

FIG. 3 shows the data from Channel B during the etch. Neither channel shows a well-defined signal drop which would indicate endpoint, as the data in both channels is dominated by an overall slow downward signal drift, as well as short-term signal fluctuations.

Figure 4:
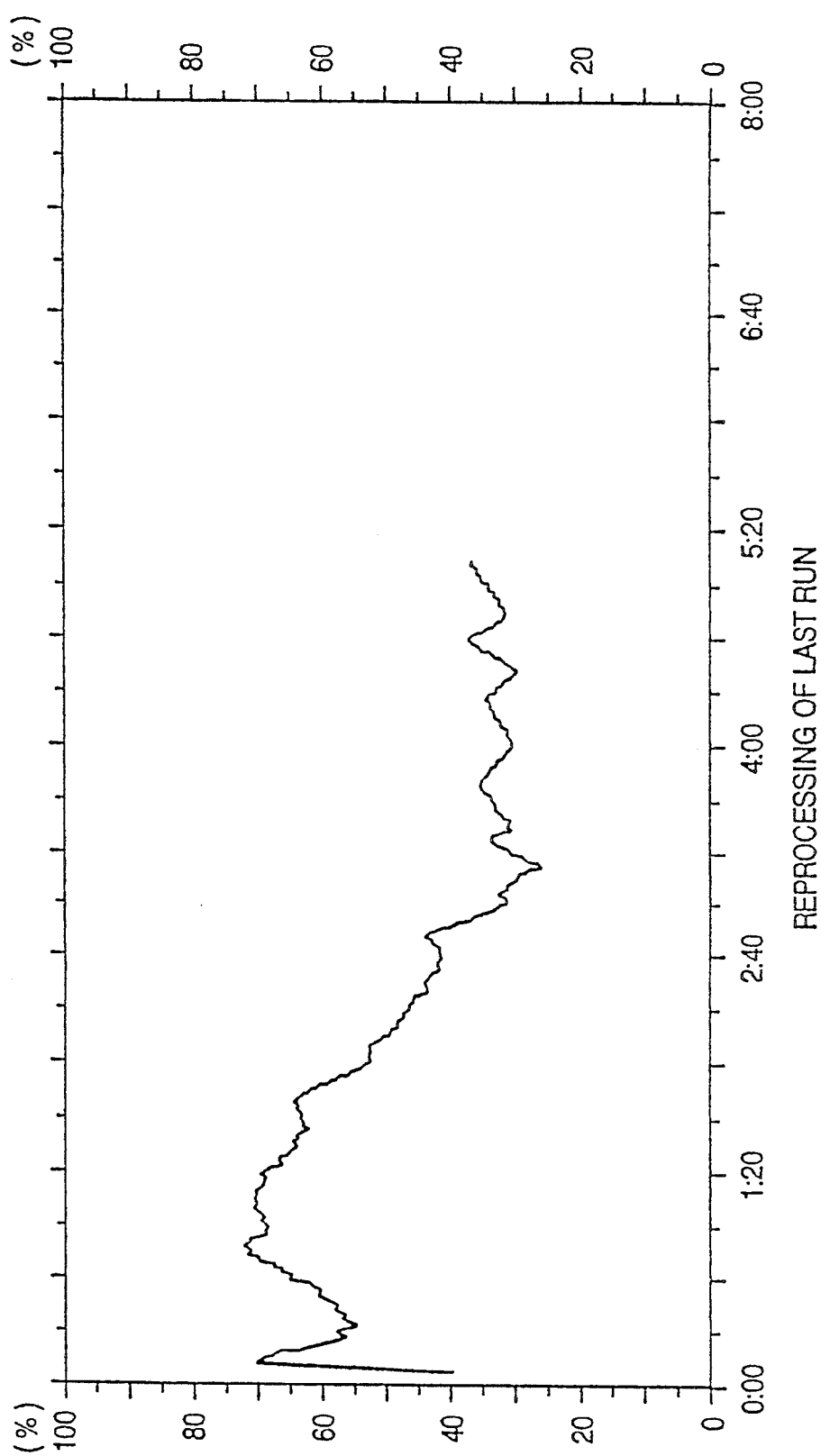
FIG. 4 is a graph of the resultant curve derived by combining the signals of FIG. 2 and FIG. 3 with an algorithm.

FIG. 4 shows the resultant curve derived by the algorithm A-(N×B), with N=1.0. The scale of FIG. 3 is expanded approximately 3 times relative to FIGS. 1 and 2. The signal drop beginning at approximately 1:20 and ending at approximately 3:20 constitutes a well-defined endpoint curve that can be easily recognized by the endpoint detector's slope detection software. The algorithm has successfully removed interferences and revealed the true endpoint curve. Once the endpoint is detected, the device can send an output control signal to the etcher to terminate the etch or to initiate a-process change.

We claim:

1. In an optical emission detection method which converts a light emission intensity to a measurable electrical signal for monitoring a dry etch process for microfabrication, an improved method for minimizing interferences comprising the steps of:
   (a) measuring said electrical signal in separate channels at two or more wavelengths, thereby generating a plurality of separate electrical signals;
   (b) normalizing the separate electrical signals from said separate channels;
   (c) analyzing said Separate electrical signals for random noise, correlated fluctuations, and a dry process monitoring signal;
   (d) maximizing the signal to random noise ratio of the dry process monitoring signal;
   (e) minimizing the obscuring effects of correlated fluctuations from the separate channels by algorithms; thereby providing a resultant signal which is no longer obscured by random noise or correlated fluctuations.

2. A method in accordance with claim 1, wherein said dry etch process is a plasma etch which includes periodic modulations of the plasma.

3. A method in accordance with claim 2, wherein said separation of channels is effected by a fiber optics bundle having two or more sets of fibers.

4. A method in accordance with claim 3, wherein the fibers within said sets are mixed so as to minimize any bias in the view of each fiber bundle.

5. A method in accordance with claim 1, wherein an exposed film area of a surface to be etched is less than 5% of the surface.

6. A method in accordance with claim 1, wherein digital processing is used to maximize the signal to random noise ratio.

7. A method in accordance with claim 1, wherein the raw measurable electrical signal includes a noise portion, and wherein the method includes the step of obtaining a useful resultant signal from said noise portion of the raw signal prior to the step maximizing the signal to random noise ratio of the dry process monitoring signal.

8. A method in accordance with claim 1, wherein said interferences are periodically varying low frequency modulations of plasma and wherein said minimizing step includes the step of averaging said separate electrical signals over an integral number of plasma modulation cycles.

9. A method in accordance with claim 1, wherein said interferences are periodically varying low frequency modulations and wherein said minimizing step includes the step of filtering said separate electrical signals in order to minimize said low frequency modulations.

10. In an optical emission detection method which converts a light emission intensity to a measurable electrical signal for monitoring a dry etch process for microfabrication, an improved method for minimizing interferences comprising the steps of:
    (a) measuring said electrical signal in separate channels at two or more wavelengths;
    (b) reducing levels of random noise in the electrical signal so that correlated fluctuations within the electrical signal become detectable and thereby become removable; and
    (c) combining signals from said separate channels in a manner to minimize obscuring effects of correlated fluctuations within said separate channels; thereby producing a resultant signal which is no longer obscured by random noise or correlated fluctuations.

11. A method in accordance with claim 10, wherein said separation of channels is effected by a fiber optics bundle having two or more sets of fibers.

12. A method in accordance with claim 11, wherein the fibers within said sets are mixed so as to minimize any bias in the view of each fiber bundle.

13. A method in accordance with claim 10, wherein said dry etch process is a plasma etch which includes periodic modulations of the plasma.

14. A method in accordance with claim 13, wherein said separation of channels is effected by a fiber optics bundle having two or more sets of fibers.

15. A method in accordance with claim 13, wherein the fibers within said sets are mixed so as to minimize any bias in the view of each fiber bundle.

16. A method in accordance with claim 10, wherein the exposed film area of a surface to be etched is less than 5% of the surface.

17. A method in accordance with claim 10, wherein digital processing is used to maximize the signal to random noise ratio.

18. A method in accordance with claim 10, wherein the measurable electrical signal contains a noise portion and a nonnoise portion, and wherein a useful resultant signal is provided from the non-noise portion of the electrical signal.

19. A method in accordance with claim 10, wherein said interferences are periodically varying low frequency modulations of plasma and said separate electrical signals are averaged over an integral number of plasma modulation cycles.

20. The method of claim 10 further comprising the step of normalizing the separate electrical signals from said separate channels.

21. The method of claim 10 further comprising the step of analyzing said electrical signal for random noise, correlated fluctuations, and dry process monitoring signal.

22. The method of claim 10 wherein said measuring step includes the steps of:

attuning a first channel of said separate channels to receive a random noise signal component, a correlated fluctuation signal component, and an endpoint signal component; and attuning a second channel of said separate channels to receive a random noise signal component and a correlated fluctuation signal component, but not an endpoint signal component;

thereby causing said first channel to comprise said endpoint signal component, and causing said second channel to be devoid of said endpoint signal component.

23. The method of claim 10 wherein said correlated fluctuations include changes due to modulations of a plasma.

24. A method in accordance with claim 10, wherein said interferences are periodically varying low frequency modulations and wherein said combining step includes the step of filtering said separate electrical signals in order to minimize said low frequency modulations.

25. The method of claim 24 wherein said filtering step includes the step of averaging said separate electrical signals over an integral number of periodic modulation cycles.

26. In an optical emission detection method which converts a light emission intensity to a measurable electrical signal for monitoring a dry etch process for microfabrication, an improved method for minimizing interferences comprising the steps of:

(a) measuring said electrical signal in a first separate channel including at least one first wavelength;

(b) measuring said electrical signal in a second separate channel including at least one second wavelength, wherein said first wavelength is different from said second wavelength;

(b) reducing levels of random noise in the electrical signal so that correlated fluctuations within the electrical signal become detectable and thereby become removable; and (c) combining signals from said separate channels in a manner to minimize obscuring effects of correlated fluctuations within said separate channels; thereby producing a resultant signal which is no longer obscured by random noise or correlated fluctuations.

27. The method of claim 26 wherein said reducing step includes the step of analyzing said electrical signal for random noise, correlated fluctuations, and a dry process monitoring signal.

28. The method of claim 26 wherein said reducing step includes the step of normalizing the separate electrical signals from said separate channels.

* * * * *

UNITED STATES PATENT AND TRADEMARK OFFICE
CERTIFICATE OF CORRECTION

PATENT NO. : 5,414,504
DATED : May 9, 1995
INVENTOR(S) : Litvak et al.

It is certified that error appears in the above-indentified patent and that said Letters Patent is hereby corrected as shown below:

In Column 7 at line 59 in Claim 1 replace:
   "(c) analyzing said Separate electrical signals for ran-" with --(c) analyzing said separate electrical signals for ran- --

In Column 9 at line 20 in Claim 21 replace:
   "correlated fluctuations, and dry process monitoring" with --correlated fluctuations, and a dry process monitoring--

Signed and Sealed this

Fourteenth Day of May, 1996

*Attest:*

BRUCE LEHMAN

*Attesting Officer*     *Commissioner of Patents and Trademarks*